(12) United States Patent
Rosato et al.

(10) Patent No.: US 8,173,153 B2
(45) Date of Patent: May 8, 2012

(54) SKIN-CARE COMPOSITIONS

(75) Inventors: Pietro Rosato, Dusseldorf (DE); Rainer Lange, Köln (DE); Johannes Crotogino, Düsseldorf (DE)

(73) Assignee: Johnson & Johnson GmbH (DE)

( * ) Notice: Subject to any disclaimer, the term of this patent is extended or adjusted under 35 U.S.C. 154(b) by 245 days.

(21) Appl. No.: 12/327,913

(22) Filed: Dec. 4, 2008

(65) Prior Publication Data

US 2009/0181060 A1   Jul. 16, 2009

(30) Foreign Application Priority Data

Dec. 14, 2007  (EP) ..................... 07024339

(51) Int. Cl.
*A61F 13/00* (2006.01)
*A61K 8/02* (2006.01)

(52) U.S. Cl. ...................... 424/443; 424/401

(58) Field of Classification Search .............. None
See application file for complete search history.

(56) References Cited

U.S. PATENT DOCUMENTS

| | | | |
|---|---|---|---|
| 5,869,075 A * | 2/1999 | Krzysik | 424/414 |
| 2004/0131660 A1 | 7/2004 | Lange et al. | |
| 2005/0008681 A1 | 1/2005 | Deckner et al. | |
| 2005/0136098 A1 | 6/2005 | Spadini et al. | |
| 2006/0233866 A1 * | 10/2006 | Hauser et al. | 424/443 |
| 2006/0257349 A1 * | 11/2006 | McLaughlin et al. | 424/73 |
| 2007/0026028 A1 | 2/2007 | Close et al. | |

FOREIGN PATENT DOCUMENTS

| | | |
|---|---|---|
| DE | 19805433 A1 | 8/1999 |
| DE | 19906081 A1 | 8/2000 |
| EP | 1757261 A3 | 6/2008 |
| WO | WO9630576 | 10/1996 |
| WO | WO02056841 | 7/2002 |
| WO | WO02056842 | 7/2002 |
| WO | WO02072052 | 12/2002 |
| WO | WO03037292 | 5/2003 |
| WO | WO03039492 | 5/2003 |
| WO | WO03066073 | 8/2003 |
| WO | WO2004062630 | 7/2004 |
| WO | WO2005004834 | 1/2005 |
| WO | WO2006000360 | 1/2006 |
| WO | WO2006083980 | 8/2006 |
| WO | WO2006099232 | 11/2006 |

OTHER PUBLICATIONS

European Search Report dated Sep. 4, 2008.

* cited by examiner

*Primary Examiner* — Kevin Hill
*Assistant Examiner* — Lyndsey Beckhardt

(57) ABSTRACT

In certain embodiments provided are composition suitable for cleansing or treating the skin, the composition comprising: (i) at least 90% water; (ii) a non-ionic surfactant; (iii) one or more hydrophobic emollients present in a concentration from about 200 parts per million (ppm) to about 4000 ppm, and wherein the composition has a ratio of total surfactant concentration to total hydrophobic emollient concentration that is from about 0.5 to about 2.5. In other embodiments, provided are articles comprising a water-insoluble absorbent substrate and a composition comprising a polyol polyhydroxystearate or a water-soluble glyceryl polyacrylate impregnated therein.

4 Claims, No Drawings

SKIN-CARE COMPOSITIONS

FIELD OF INVENTION

The present invention relates to skin-care compositions having low surfactant concentrations and, in particular, absorbent sheets comprising said compositions.

DESCRIPTION OF THE RELATED ART

Compositions useful for cleansing the skin and hair e.g., body washes, facial cleansers, and shampoos, are well known. Typically, such compositions include surfactants that are chosen for such characteristics as mildness to skin and eyes, foaming, and skin feel. Cleansing compositions that are coated or impregnated on wipes that are useful for cleansing the skin also generally are designed for mildness and soft-feel or conditioning, with foam performance being less important.

So-called "wet wipes" have become successful as products particularly suited for personal care applications. These products typically are manufactured by impregnating sheets made of non-woven fabric with a suitable composition. Wipes and similar products impregnated with various types of compositions have been sold commercially. Such compositions are typically high in surfactants such as betaines and/or have high concentrations of oils, e.g., mineral oils or silicone oils. Other examples in the art are disclosed in the following references:

US20040131660 describes a wipe with a water-in-oil-emulsion comprising a $C_{12-30}$ carboxylic acid mono- or diglyceride. Example compositions provided are phase inverse (PIT) emulsions, which, as is typical of PIT emulsions, have high oil concentrations and high surfactant concentrations as well. EP0808151 describes a wipe product comprising an emulsion of silicone oil and a polymeric emulsifier. Exemplary compositions include at least 5000 parts per million (ppm) of silicone oil and at least 1000 ppm of polymer.

Unfortunately, the prior art fails to provide a composition, such as one useful for impregnation onto a wipe that has the benefits such as the utilization of ingredients that are mild and obtainable from natural sources; employing rather low concentrations of ingredients to achieve cost-effective performance; and providing a soft feeling against the skin. Furthermore, particularly for baby wipes, it would be desirable to provide high degree of cleansing, such that a user does not have to wipe the skin repeatedly to remove soil, which would otherwise tend to cause skin irritation. Thus, there is a need to overcome one or more of the above-mentioned drawbacks.

SUMMARY OF THE INVENTION

In one aspect, the present invention provides a composition suitable for cleansing or treating the skin, the composition comprising: (i) at least 90% water; (ii) a non-ionic surfactant; (iii) one or more hydrophobic emollients present in a concentration from about 200 parts per million (ppm) to about 4000 ppm, and wherein the composition has a ratio of total surfactant concentration to total hydrophobic emollient concentration that is from about 0.5 to about 2.5. Also provided are articles, such as wipes comprising a water insoluble absorbent substrate impregnated with said compositions. Processes for preparing said compositions, articles comprising such compositions as well as uses of such compositions and articles are also provided for.

In another aspect, the present invention provides an article, such as a wipe, comprising a water-insoluble absorbent substrate and a composition comprising a polyol polyhydroxytearate or a water-soluble glyceryl polyacrylate impregnated therein. Processes for preparing such articles as well as uses of such articles are also provided for.

DESCRIPTION OF PREFERRED EMBODIMENTS

All percentages listed in this specification are percentages by weight, unless otherwise specifically mentioned. Whenever used in this description and claims, any concentration (in percentage or parts per million(ppm)) is weight by weight (w/w). Percentages are further meant to define the concentration of "active ingredient," i.e., excluding water and other ingredients that are not the particular ingredient in question. The term "substantially free" as applied to various types of ingredients, unless otherwise specified, means the ingredient is present in a concentration of less than about 0.5%, more preferably less than about 0.1%, and even more preferably less than about 0.01% (100 ppm).

The compositions are able to provide various benefits even though the composition is, in certain embodiments, highly dilute. As such, the compositions may include at least about 90% water. In certain preferred embodiments, the percentage of water is from about 95% water to about 99.5% water, such as from about 97% water to about 99% water.

Compositions of the present invention, although dilute, further include one or more hydrophobic emollients and a non-ionic surfactant. In certain embodiments, the composition further has a total surfactant to total hydrophobic emollient in a weight-to-weight ratio that is from about 0.5 to about 2.5; a total hydrophobic emollient concentration from about 200 ppm to about 4,000 ppm. In other embodiments, an article comprises (1) a water-insoluble absorbent substrate and (2) a composition comprising a polyol polyhydroxystearate and/or a water-soluble glyceryl polyacrylate impregnated therein.

In one embodiment the composition of the invention comprises water, an non-ionic surfactant, and one or more hydrophobic emollients present in a concentration of at least 200 ppm, in particular from about 200 ppm to about 4,000 ppm, and wherein the composition in particular a ratio of total surfactant concentration to total hydrophobic emollient concentration that is from about 0.5 to 2.5.

Surprisingly, the compositions of the present invention are phase stable and have both excellent cleansing properties and aesthetics.

Surfactant

Compositions of the present invention include one or more surfactants. By "surfactant," it is meant any of those molecules that are commonly known in the art to provide a reduction in surface tension (such as being able to reduce the surface tension of water to 50 dynes/cm or less, and, more preferably 45 dynes/cm or less when added to pure deionized water, and measured at ambient temperature i.e., 20° C.). Furthermore, it is preferred that the surfactant or surfactants have a water solubility of at least about 1% in deionized water at ambient temperature. As such, the term surfactant can also include those molecules that are also commonly referred to as oil in water emulsifiers. In one embodiment, the non-ionic surfactant has a Hydrophile-Lipophile Balance (HLB) that is from about 8 to 14, and more preferably from about 10 to about 14.

Although the composition may include surfactants of various types, e.g., non-ionic, anionic, amphoteric, cationic, or mixtures thereof, in a preferred embodiment, compositions of the present invention include a non-ionic surfactant. By "non-ionic surfactant," it is meant a surfactant that does not ionize in aqueous media. In a preferred embodiment, the non-ionic surfactant is liquid at ambient temperature.

The function of the surfactant is to provide one or more of the following: emulsification or solubilization of hydrophobic compounds, wetting, surface tension reduction, or detergency.

One particularly suitable type of nonionic surfactant are long chain, fatty alkyl glycosides such as polyglucosides, which are the condensation products of (a) a long chain alcohol containing from about 6 to about 22, and preferably from about 8 to about 14 carbon atoms, with (b) glucose or a glucose-containing polymer. Particularly notable polyglucosides are $C_{8-20}$ alkyl glucosides, more in particular a $C_{8-16}$ alkyl glucoside, preferably coco-glucoside.

As used herein $C_{8-20}$ alkyl or $C_{8-20}$ alkyl refers to straight or branch chained hydrocarbon radicals, saturated or unsaturated, having from about 8 to about 20 or from about 8 to about 16 carbon atoms, including mixtures thereof. $C_{8-20}$ alkyl or $C_{8-16}$ alkyl in particular is derived from fatty alcohols. Examples of $C_{8-16}$ alkyl are capryl, 2-ethylhexyl, caprinyl, lauryl, isotridecyl, myristyl, palmoleyl, cetyl, and the like. $C_{8-20}$ alkyl comprises these radicals as well as stearyl, isostearyl, oleyl, linolenyl, linolyl, and the like.

The term 'alkyl glucoside' generally is used in the art to refer to alkylated mono- or polyglucosides (also referred to as oligoglucosides to account for varying degrees of polymerization) or mixtures thereof. The latter also includes alkylation products of technical mixtures of glucosides. The average number of glucose units in the glucosides can be represented by an index number that usually is referred to as 'oligomerisation grade'. Typical oligomerisation grades are in the range of 1 to 10, in particular in the range of 1 to 6, more in particular in the range of 1 to 3. Preferred oligomerisation grades are in the range of 1.1 to 3, or less than 1.7, more preferred grades are in the range of 1.2 to 1.4. Alkyl glucosides and preparation processes are described for example in WO-01/09153. The alkyl glucosides can be obtained by reacting a suitable alcohol with glucose. In this reaction, glucose molecules may react with each other thus forming polyglucosides. By controlling the reaction conditions the amount and nature of polyglucosides in the end product can be controlled.

One particularly preferred polyglucoside that has excellent mild detergency and skin-feel is a cocoglucoside commercially available from Cognis Corp of Ambler, Pa. and sold under the trademark LAMESOFT, in particular LAMESOFT PO65', a mixture of about 34% of $C_8$-$C_{18}$ cocoglucoside that is blended with the hydrophobic emollient—glyceryl monooleate, and water. Another preferred cocoglucoside is PLANTACARE 818 UP, a 50% cocoglucoside in water.

Another preferred polyglucoside that has excellent ability to emulsify hydrophobes in an aqueous system as well as skin-feel is a lauryl glucoside also commercially available from Cognis and sold under the trademark EMULGIN VL75, a mixture of 25% lauryl (predominantly C12) glucoside that is blended with a polyglycerolpolyhydroxystearate and water.

In order to steadily more demanding regulatory standards, the composition need not include non-ionic surfactant that may have residual ethylene oxide. As such while in certain embodiments these surfactants may be included in the composition of the present invention, in certain preferred embodiments, the composition is free of non-ionic surfactants that are substantially free of alkoxylated moieties. Examples of such non-ionic surfactants that may be excluded are fatty alcohol acid or amide ethoxylates, monoglyceride ethoxylates, primary or secondary alcohol or alkylphenolethoxylates, and other surfactants that including repeating ether units other than polyglycosides.

As further examples of nonionic surfactants having alkoxylated moieties that may be excluded from the composition are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Uniqema of Chicago, Ill. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

The amount of the non-ionic surfactant in the composition in particular is less than about 0.4% (4000 ppm), preferably from about 100 ppm to about 3000 ppm, more preferably from about 200 ppm to about 2000 ppm, and even more preferably from about 500 ppm to about 2000 ppm.

In certain embodiments, the composition of the present invention includes one or more charged surfactants. The charged surfactant may be an anionic surfactant typically employed in personal care compositions, e.g., alkyl ether sulfates, sulfosuccinates, isethionates, sulfoacetates, and the like. In another embodiment, the charged surfactant is an amphoteric surfactant, i.e., one capable of assuming multiple states of different charge dependent upon pH. Examples include betaines, amphocarboxylates such as alkylamphoacetates (mono or di); phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl γ-aminoproprionic acids; alkylpolyamino carboxylates; and mixtures thereof.

The charged surfactant may be a cationic surfactant such as alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, such as about 8 to about 22.

In order to reduce potential irritation of the composition, in one embodiment, the composition is substantially free of anionic surfactants. In another embodiment, the composition is substantially free of all charged surfactants.

In certain preferred embodiments, compositions of the present invention have a total concentration of surfactant, i.e., the sum concentration of all surfactants in the composition that is from about 100 ppm to about 0.4% (4000 ppm), preferably from about 100 ppm to about 3000 ppm, more preferably from about 200 ppm to about 2000 ppm, and even more preferably from about 500 ppm to about 2000 ppm.

Hydrophobic Emollient

In order to provide acceptable skin-feel as well as softness and smoothness, and moisture retention, compositions of the present invention include one or more hydrophobic emollients. The one or more hydrophobic emollients are generally either not surface active (as determined using the definition for surface tension reduction above) or if they are surface active have a low HLB (such as less than about 7, preferably less than about 5), have little to no water solubility (e.g., less than about 0.50% will dissolve in deionized water at ambient temperature), have molecular weights greater than about 200, such as greater than about 250, such as between about 250 and about 500; and, in one embodiment, are fluid at ambient temperature. Furthermore the hydrophobic emollient is not substantially volatile at ambient temperatures, unlike, for example, fragrance oil components (e.g., limonene, benzyl alcohol, pinene, cedrene, camphor, terpinene, and the like), that typically have high vapor pressures.

Examples of suitable hydrophobic emollients include, but are not limited to mineral oils, fatty ($C_8$ or greater, preferably $C_{12}$ or greater) alcohols, alkanols, or esters; vegetable oils, glycerol esters of fatty acids (including mono-, di- or triglycerides); lanolin alcohol, acid or related derivatives thereof, tocopherols; aloins, non-hydrocarbon based oils such as dimethicone, silicone oils, silicone gums, and the like.

Particularly preferred hydrophobic emollients are esters of fatty (carboxylic) acids. The fatty acid portion may have a carbon chain length from about $C_{12-30}$. The term $C_{12-30}$ carboxylic acid is meant to comprise pure acids or mixtures thereof. The carbon chain may be linear or branched; saturated or unsaturated (i.e., having one or more double bonds). They fatty acid component may also contain one or more, e.g. two, hydroxy groups. These acids comprise the so-called fatty acids, i.e. acids derived from naturally occurring fats.

Particularly preferred hydrophobic emollients are esters of fatty acids and glycerol. In one embodiment, the hydrophobic emollient is a triglyceride, but, in certain embodiments, the composition is free of triglycerides. In a preferred embodiment the hydrophobic emollient is a mono- or diglyceride, such as a $C_{12-30}$ mono- or diglyceride or a mixture thereof, such as linear, saturated $C_{12-30}$ mono- or diglyceride. The quantity of mono- and/or diglyceride in such mixture may vary, it can be between 0 and 100%. Preferred are mixtures that contain more than 50% of monoglyceride, in particular more than 70% of the latter. Of particular note are compositions in which the ester of glycerol and fatty acid is at least 80%, in particular at least 90%, more in particular at least 95% or even at least 99% of $C_{12-30}$ carboxylic acid monoglyceride.

In one embodiment, the diglyceride includes two different carboxylic acid rests. These mixed diglycerides also comprise (mono-$C_{12-30}$ carboxylic acid) (mono-oleic acid) glycerides. An example thereof is (mono-palmitoleic acid) (mono-oleic acid) glyceride.

Preferably the carboxylic acid has from about 16 to about 22 carbon atoms, more preferably from about 16 to about 20 carbon atoms, still more preferably from about 16 to about 18 carbon atoms. Of particular interest are those containing 18 carbon atoms. A particularly preferred ester of glycerol and fatty acid is glyceryl mono- or dioleate. One particularly preferred ester of glycerol and fatty acid that has excellent mildness and skin-feel is a glyceryl monooleate (HLB of approximately 3.8) that is commercially available from Cognis Corp of Ambler, Pa. and sold under the trademark LAMESOFT, in particular LAMESOFT PO65', a mixture of about 31% glycerol monooleate that is blended with $C_8$-$C_{18}$ coco glucoside and water.

Compositions of the present invention have a total concentration of hydrophobic emollient, i.e., the sum concentration of all hydrophobic emollient in the composition that is from about 200 ppm to about 0.4% (4000 ppm), preferably from about 300 ppm to about 3000 ppm, more preferably from about 400 ppm to about 2000 ppm, and even more preferably from about 500 ppm to about 1000 ppm.

In certain embodiments, the composition has a ratio of total surfactant to total hydrophobic emollient that is from about 0.5 to about 2.5, such as from about 0.75 to about 2.2, such as from about 1.0 to about 2.0.

Hydrophobic Polymers and Waxes

The composition of the present invention may further include hydrophobic molecules having little to no water solubility (e.g., less than about 0.25% will dissolve in deionized water at ambient temperature) that are solid at ambient temperature. However, it is generally desirably that the concentration of these species are present in low amounts, or otherwise they may destabilize the composition. In one embodiment, the concentration of such compounds is less than about 0.25%, preferably less than about 0.1%, and, more preferably less than about 500 ppm. In another embodiment, the concentration of the hydrophobic polymer or wax is present in a concentration from about 100 ppm to about 2500 ppm, such as from about 200 ppm to about 1000 ppm.

Suitable hydrophobic polymers that include various synthetic (e.g, water insoluble acrylics, polyesters and the like) or natural polymers that are cosmetically acceptable and meet the low solubility requirement above. One particularly suitable hydrophobic polymer are glyceryl esters of polystearates, such as polyol polyhydroxystearates that are made by esterifying polyhydroxystearaic acid with a degree of self-condensation of 2 to 10 with a polyglycerol mixture (glycerol, diglycerols, triglycerols, tetraglycerols, pentaglycerols, and mixtures thereof). Suitable examples are described in U.S. Pat. No. 6,264,961. One such example is polyglyceryl 2-dipolyhydroxystearate, commercially available from Cognis Corp and sold under the trademark as EMULGIN VL-75, a mixture of a mixture of about 25% polyglyceryl 2-dipolyhydroxystearate that is blended with lauryl glucoside, glycerin and water.

Waxes that may be included in the composition include hydrocarbon and/or silicone waxes that may or not reduce surface tension as much as a non-ionic surfactant, but are suitable emulsifiers—examples include such as cetearyl alcohol/ceteareth 20, cetearyl alcohol, and glyceryl stearate. Other suitable waxes include those cosmetic waxes that melt near body temperature, such as those sold under the trade name CAREMELT from Cognis Corp.

Humectants

Compositions of the present invention may further include humectants, i.e., compounds that have relatively high water solubility (generally greater than about 5% by weight in deionized water at ambient temperature) and are hygroscopic, and function to absorb and hold water against the skin.

Suitable humectants include glycerol, glyceryl triacetate, sorbitol, xylitol maltitol, low carbon chain diols such as propylene glycol, polymeric polyols like polydextrose, or natural extracts like quillaia, or lactic acid or urea. In an a preferred embodiment, the humectant is glycerol or sorbitol, and, most preferably glycerin.

The concentration of humectant in the composition, if included, may be from about 0.05% (500 ppm) to about 5%, preferably from about 0.1% to about 2%, more preferably from about 0.2% to about 0.5%.

Water-Soluble Polymers

Compositions of the present invention may include one or more water-soluble polymers. The water-soluble polymer may have a solubility that is greater than about 2% by weight in deionized water, or in a 50:50 weight:weight mixture of water: glycerin, at ambient temperature). The water-soluble polymer may have a molecular weight of greater than about 1000, preferably having a molecular weight about 2000, such as above about 3000. In certain embodiments, the polymer is crosslinked. The water-soluble polymer may serve one or more of the following functions: skin-conditioning, viscosity modification, phase stabilization, or film-formation.

The water-soluble polymer may be a natural polymer such as a protein or polysaccharide. For example, the water-soluble polymer may be a protein or protein hydrolyzate, such as an extract of milk, wheat or other cereals or of leguminous plants and of oleaginous plants, such as extracts of corn, rye, *Triticum aestivum*, buckwheat, sesame, *Triticum spelta*, pea, bean, lentil, soybean and lupin.

Suitable polysaccharides and derivatives include those derived from the polymerization of rings of D-glucopyranose, D-glucose, D-galactose, D-mannose, D-xylose or other saccharides. The polysaccharide may be derived from algae or plants, and may include, for example, starches, glycogen, cellulose, amylopectin, amylase, xylan, gum tragacanth, inulin, laminarin, mannan, or guar. The polysaccharides derived from algae or plants include cationic polysaccharides such as naturally occurring polysaccharides that have been derivatized to create cationic character, e.g. quaternization with various quaternary amine compounds containing reactive chloride or epoxide sites.

In another embodiment of the invention, the water-soluble polymer is a synthetic polymer. Suitable synthetic polymers include, for example, acrylic polymers with or without hydrophobic modification, polyurethanes, polyurethane-acrylics, vinyl polymers such as polyvinyl alcohol polyvinylpyrolidone, polyurethane-polyvinylpyrrolidones, polyester-polyurethanes, polyether-polyurethanes polyacrylamides, polyureas, polysulfonates, poly(2-ethyl-2-oxazoline), and mixtures thereof.

One particularly suitable water-soluble polymer is a water-soluble glyceryl polyacrylate, and, in particular, a glyceryl polymethacrylate, such as those commercially available from Cognis Corp under the trade name HISPAGEL 200, which is a 3% solution of glyceryl polymethacrylate blended with glycerin and water. Another particularly suitable water-soluble polymer is a crosslinked polyacrylate, and, in particular, a crosslinked polyacrylate commercially available from Lubrizol Advanced Materials of Cleveland, Ohio and sold under the trade name CARBOPOL ULTREZ 10, which is a 100% solids of crosslinked polyacrylate. Another particularly suitable water-soluble polymer is a carboxymethylcellulose polymer commercially available from Hercules Inc. of Wilmington, and sold under the trade name NATROLSOL 250HR.

The concentration of water-soluble polymer in the composition, if included, may be from about 25 ppm to about 5000 ppm, preferably from about 300 ppm to about 3000 ppm, and more preferably from about 500 ppm to about 2500 ppm, and even more preferably from about 1000 ppm to about 2500 ppm.

Other Ingredients

Compositions of the present invention may include other ingredients as long as they do not adversely affect the phase stability or significantly and adversely affect the aesthetics or cleansing ability of the composition. For example, the composition may include preservatives such as sodium benzoate, cinnamic acid, methoxybenzoic acid (p-anisic acid), or phenoxyethanol, in concentrations such as from about 100 ppm to about 20,000 ppm, preferably from about 500 ppm to about 5000 ppm. The composition may also include pH adjusters such as alkali metal hydroxides or inorganic or organic acids (e.g., citric acid) in concentrations that may be from about 100 ppm to about 5000 ppm.

The compositions may further contain anti-oxidants in particular in case where the an unsaturated $C_{12-30}$ carboxylic acid is included in the composition. Suitable anti-oxidants are agents that block oxidation or autoxidation of the components in the compositions for use in the products of the invention, in particular of the $C_{12-30}$ carboxylic acid mono- or diglyceride component. Examples of anti-oxidants are e.g., tocopherol or derivates thereof, vitamin E or derivatives thereof, ascorbic acid or derivates thereof, citric acid, propyl gallate, chitosan glycolate, cysteine, N-acetyl cysteine plus zinc sulfate, thiosulfates, e.g., sodium thiosulfate, polyphenoles, tocopherol, butylhydroxytoluene (BHT), butylhydroxyannisol (BHA), lecitine, and the like.

Other classes of ingredients, such as those discussed below in the remainder of this section on "Other ingredients" may be included in the composition in order to provide additional functionality. However, in certain embodiments, in order to either (1) reduce the burden of maintaining phase stability and/or (2) make the composition suitable for use on sensitive skin such as the skin of a baby, the composition may be free of one or more of the following classes of ingredients: agents, particularly amine-containing agents (e.g, EDTA, phosphates and the like) that are suitable for sequestering such ions as calcium, magnesium, or iron; dyes and pigments; and oxidizing and reducing agents. The composition may exclude biologically-active benefit agents such as sunscreen agents, anti-acne agents, skin darkening/tanning agents, anti-acne agents, anti-microbial agents, anti-inflammatory agents, antifungals, external analgesics, sunscreens, photoprotectors, keratolytic agents, hair growth inhibitors, anti hair-loss agents, hair growth promoters, hair removers, skin-firming agents, allergy inhibitors, antihistamines, sensates; sunscreens; anti-edema agents; and combinations thereof. In yet another embodiment, the composition may have less than 1% or be substantially or completely free of volatile solvents such as lower alcohols such as ethanol or isopropanol.

The compositions in the products of the invention in particular are liquid compositions. They generally exist in the form of a solution or a slightly turbid oil-in-water emulsion.

The composition has a pH that is generally suitable for contact with human skin, such as from about 4.5 to about 7.5 The viscosity of the composition is varied, such as by adjusting the levels of water-soluble polymer, but may be less than about 10,000 centipoise when measured using a LVT3 spindle at 30 rpm.

Compositions of the present invention may be made, for example, charging a vessel with water and mixing the various ingredients under agitation. For example, the water-soluble polymer may be added to the water, which is then agitated, sufficient alkali metal hydroxide is added to increase the pH to about 4.9 to about 5.2. Then a premix of all humectants, hydrophobic emollients, surfactants may be separately mixed at a temperature between ambient to about 50° C. and stirred for a time sufficient to homogenize the premix; the premix is then added to the water/polymer mixture and allowed to stir for a time sufficient to homogenize the mixture; then preservative is added and then the pH is adjusted to bring the pH down to the correct level.

Absorbent or Porous Sheet

In one preferred embodiment, the composition of the present invention is impregnated or absorbed on an absorbent or porous sheet such as is commonly called a "wipe." The main functions of wipe are to provide a convenient delivery form for the composition, and/or to assist in soil removal and/or to provide softness against the skin of the user. The sheet of absorbent or porous material for use in the products of this invention may take the form of a tissue, a wipe, towel, towelette, and the like. The material may be flushable. As used herein, by 'flushable' is meant that the material will pass through at least 3 meters of waste pipe in two toilet flushes. The material may also biodegradable.

The amount of the composition on the sheet will be in the range from about 100% to about 400%, preferably from about 200% to about 400%, expressed as the weight of the composition relative to the weight of the sheet in dry condition. While these so-called "wet wipes" are the preferred form for delivering compositions of the present invention, in certain embodiments, coatings on nonwovens of these compositions to create "dry-wipes" or cover materials suitable for diapers or feminine hygiene articles are also contemplated.

Sheet materials that can be used include those that are mono or multi-layered, woven or non-woven. They can be made of one or of several materials. Particularly preferred are non-woven materials that have a web structure of fibrous or filamentous nature, in which the fibres or filaments are distributed randomly or with a certain degree of orientation. For example, web formation of the nonwoven may include one or more of the air-laying, drylaing, spunlayingor wet-laying technique. Web bonding of the nonwoven may include chemical, thermal or mechanical techniques.

In a preferred embodiment of the present invention, the carrier material is made by the so-called spunlace technique, which is dry laying (carding) by subsequent hydroentanglement. The fibres or filaments can be natural, for example wood pulp, wool cotton, linen and the like, or synthetic, for example polyvinyls, polyesters, polyolefins, polyamides and the like.

Typically they have a weight per square meter in the range of 10 to 80 g/m$^2$, in particular of 20 to 70 g/m$^2$. Particularly preferred materials are of the non-woven type. Based on the raw material that has been used, two different types of products can be distinguished.

A first type of carriers is paper based. The raw materials for these carriers are made almost exclusively of cellulose-based fibres or filaments from plant cellular sources (pulp). These can be available from fresh wood-shavings or from recycled material (recycled paper). In a number of wipe applications, such as baby wipes, wipes for cleansing, wet paper towels and the like, high wet strength or firmness of the non-woven web is a desirable attribute. This can be achieved by the addition of binding materials. Examples of such materials are the so-called wet strength resins. In some cases additives are added in order to increase the softness of the end product. In a second type use the web is made mainly of staple fiber, e.g. based on cotton, wool, linen and the like.

Commercial products are made of cellulose fibers, synthetic fibers or mixtures of both. Polyester and polypropylene are known as suitable polymers for the preparation of synthetic fibers. Also in these products binders can be used to increase the firmness of the non-woven fabric.

Webs of increased strength can be obtained by using the so-called spunlace or hydro-entanglement as bonding technique. In this technique the individual fibers are twisted together so that an acceptable strength or firmness is obtained without using binding materials. The advantage of the latter technique is the excellent softness of the non-woven material.

Non-woven materials that are made of a mixture of pulp and staple fiber are also known. Such materials are available with binding materials, in particular those mentioned above, or without binding materials. In the latter instance the non-woven is preferably bonded by the spunlace or hydro-entaglement procedure.

In a preferred embodiment of the present invention, the carrier material is made of cellulose pulp with a small amount of binding material. The amount of binder in the carrier material is in the range of 5 to 20% (w/w).

In a particularly preferred embodiment the non-woven fabric is prepared by the water entanglement procedure and does not contain binding material.

The absorbing ability of the carrier material is of particular interest with regard to the applications envisaged by the present invention. During production the impregnating solution should be taken up quickly by the carrier. In certain embodiments of this invention the wipes will be packed in a stack of a plurality of wipes. In this instance the absorbing ability of the non-woven fabric should be such that a chromatographic effect (sinking down of the lotion) in the stack is avoided during storage. On the other hand it should be guaranteed that during the usage of the wipe the lotion is delivered evenly to the skin.

The absorbing capacity of the carrier material is determined essentially by three different parameters: the surface weight of the carrier material, the nature of the raw material used in the manufacture and the manufacturing process used.

For the applications according to the invention the carrier materials typically have a surface weight from 10 g/m$^2$ to 80 g/m$^2$, preferably from 30 to 70 g/m$^2$ and more preferably from 40 to 60 g/m$^2$. The selection of the raw material of which the non-woven carrier is made depends on the manufacturing procedure. Typically in the manufacture of non-woven carriers by the hydro-entanglement process, use is made of mixtures of cellulose fibers and synthetic fibers. The relative quantity of synthetic fibers in the non-woven fabric is from 0% to 100% and preferably is between 10% and 80%, more preferably in the range of 30% to 80%.

In order to impregnate the composition onto the absorbent sheet, the sheet material may be cut into strips in which the transversal size of which being similar to the size of the ultimate sheet, in particular the tissue or wipe. Subsequently the sheet is folded according to methods generally known and applied in the art. The thus folded strips are moistened with a liquid composition as defined herein, said moistening preferably comprising spraying or dripping. Or the fabric strips can first be moistened and subsequently be folded.

The strips can also be impregnated with the composition by immersing in or running the strip through a bath containing the composition. They can also be sprayed or printed with the composition.

In a further step, the strips are cut so that the desired size of the sheets, in particular of the wipes, is obtained. The thus obtained sheets (or wipes) can be packed individually or can be stacked in a determined number, e.g., a number between 10 and 30, preferably between 15 and 25, most preferably about 20, or a number between 50 and 100, preferably between 60 and 80, most preferably about 72, and the stack then packed in a suitable package, for example a plastic wrap, box and the like.

The products having the composition of the present invention impregnated therein can take the form of baby or adult wipes and can be used in a wide range of applications as personal care products, comprising, for example, baby cleansing wipes, face or body cleansing wipes, wipes for make-up removal, wipes for skin treatment or skin conditioning such as for example skin moisturization, insect repellent wipes, sun protection wipes, and the like.

The products of the present invention have superior softness, cleansing, and can be made in a cost-effective manner.

EXAMPLES

Example I

The test products detailed in Table 1 were evaluated by consumers for cleansing and mildness using the methodology below: A blind consumer study was conducted by allowing mothers of baby's aged 0-36 months to take home one of the following products for 7 days. At least 50% of the population recruited described themselves as inclined to use "Sensitive skin" products. Each product was evaluated by approximately 200 mothers. The users were surveyed and asked various questions including: (1) Would you categorize your satisfaction with the cleansing of he product as the product as "very satisfied," "fairly satisfied," "fairly dissatisfied" or "very dissatisfied." The percent of the respondents that rated the product as very satisfied is shown in the Table 1. (2) Would you categorize the product as being extremely mild, very mild, not very mild or not mild. The percent of the respondents that rated the product as extremely mild is shown in the Table 1.

TABLE 1

Comparison of Cleansing and Mildness By Consumers

| Example | Commercial Product Identification | Description | Cleansing (% of respondents rating as "Very satisfied") | Mildness (% of respondents rating as "Extremely mild") |
|---|---|---|---|---|
| Example E1 | — | Described below in Table 2 on a spunlace wipe of about 50 g/m² | 50[6] | 27[7] |
| Comparative Example, C1 | PENATEN Fragrance Free Wipes[1] | PIT emulsion with >70% surfactant and about 15% emollient on a spunlace wipe of about 50 g/m² | 45 | 18 |
| Comparative Example, C2 | PAMPERS Sensitive Wipes[2] | Composition[4] on a spunlace wipe (80% polypropylene and 20% viscose) of about 50 g/m² | 47 | 16 |
| Comparative Example, C3 | BabyLove Wipes[3] | Composition[5] on a spunlace wipe (50% PET and 50% viscose) of about 50 g/m² | 34 | 7 |

[1]Commercially available from Johnson & Johnson of New Brunswick, NJ
[2]Commercially available from Procter & Gamble of Cincinnati, Ohio
[3]Commercially available from DM Drogeriemarkt of Karlsruhe, Germany
[4]Includes PEG-40 hydrogenated castor oil and silicone copolymer emulsifier; fatty triglycerides, aloe; estimated to have total surfactant concentration and total hydrophobic emollient concentrations both over 5000 ppm
[5]Includes cocoglucoside and betaine surfactants; octyldodecanol; estimated to have a ratio of total surfactant to hydrophobic emollient that is much higher than compositions of the present invention
[6]Significantly better than C3, 95% confidence level
[7]Significantly better than all other products tested, 95% confidence level

TABLE 2

Composition of Inventive Example, E1

| Ingredient | Percent By Weight |
|---|---|
| Water, deionized | 97.26 |
| HISPAGEL 200 | 0.2 |
| LAMESOFT PO 65 | 0.25 |
| EMULGIN VL 75 | 0.25 |
| Glycerin, 99.5% | 0.18 |
| Sodium hydroxide, 30% | 0.2 |
| Sodium benzoate | 0.5 |
| Phenoxyethanol | 0.6 |
| CARBOPOL ULTREZ 10 | 0.2 |
| DERMOSOFT 688 (p-anisic acid) | 0.06 |
| Fragrance | 0.1 |
| Citric Acid | 0.2 |

To make the composition of Inventive example, E1, detailed above in Table 2, a vessel was charged with water. The CARBOPOL was added, then agitated. Sufficient NaOH was added to increase the pH to about 4.9 to about 5.2. A premix of all glycerin, and the required amounts of LAMESOFT PO 65, HISPAGEL 200, and EMULGIN VL-75 (see Table 2 below) were separately mixed at a temperature between ambient to about 50° C. and stirred for a time sufficient to homogenize the premix. The premix was then added to the water/polymer mixture and allowed to stir for a time sufficient to homogenize the mixture; then preservative was added and then the pH was adjusted to bring the pH to between 4.9 and 5.2.

Inventive Example E1 has a total surfactant concentration of about 1425 ppm and a total emollient concentration of about 750 ppm (ratio of total surfactant to total emollient that is about 1.9). Surprisingly, despite its low concentration of surfactant and emollient, Inventive Example, E1 showed very good cleansing and excellent mildness, and furthermore, is phase stable.

Example II

The relative mildness of Inventive Example E1 compared with the other examples is further confirmed from comparative squamometry (skin cell analysis) as well. Specifically E1 was evaluated for mildness as compared to Comparative Examples C1 and C2 (these are detailed in Table 1), as well as two controls: a solution of conventional surfactant (sodium lauryl sulfate) and water.

Eleven Caucasian female volunteers, ages 43-69, with Fitzpatrick's skin, Type I-IV, and normal skin (corneometric value >60), and in good general health were recruited as subjects. For the three days immediately prior to the start of the study, the subjects did not apply any moisturizer. The inner forearm (the opposite arm relative to their handedness) for each subject was partitioned into six delimited areas. Each of the above products were wiped three times onto selected, predetermined 4 cm$^2$ portions of the volunteer's skin, three times per day. The SLS solution and the water controls were rubbed into their respective areas of the skin with cotton wool soaked with 2 ml of solution (3 times) and 1 minutes after was rinsed with 2 cotton wools soaked with 2 ml of tap water (3 times with each cotton wool) and dried with a handkerchief. This procedure was repeated daily for a two week period.

After the two week period the treatments were stopped. About 24 hours after the last treatment skin cells from each test area were stripped using a cyanoacrylate glue Cells were collected and stained with a PMS (polychrome multiple stain that was a 50/50 mixture of a solution of toluidine blue, 0.1% in ethanol, and basic fuschin, 0.5% in ethanol) by plunging the cells into the stain for 3 minutes, followed by rinsing with distilled water. They are then dried. Colorimetric measurements were performed using a Minolta Chromameter CR 300, commercially available from Konica Minolta Sensing Americas of Ramsey, N.J. Chromameter readings are taken on the skin strippings directly. For each treatment zone, 5 "L values" (whiteness-blackness), "A values" (greenness-redness), and "B values" (blueness-yellowness) readings are taken on images. Averages are calculated to yield L*, A*, and B* for the cells subject to that particular treatment. C* is calculated as square root (A*$^2$-B*$^2$). Damaged cells accept more stain and therefore have higher C* values (the stain does not significantly affect the L values) than undamaged cells. As such, the difference, L*-C* decreases with damage. The difference, L*-C* is reported as the "Coefficient of mildness" (COM), for the particular treatment.

TABLE 3

Comparison of Coefficient of Mildness (COE) Via Squamometry

| Example | Commercial Product Identification | Description | Coefficient of Mildness (COE) |
|---|---|---|---|
| Control | — | Untreated | 54.18 |
| Example E1 | — | Described above in Table 2 on a spunlace wipe of about 50 g/m$^2$ | 53.99 |
| Water | — | — | 51.87 |
| Comparative Example, C2 | PAMPERS Sensitive Wipes[2] | Composition[3] on a spunlace wipe (80% polypropylene and 20% viscose) of about 50 g/m$^2$ | 51.68 |
| Comparative Example, C1 | PENATEN Fragrance Free Wipes[1] | PIT emulsion with >70% surfactant and about 15% emollient on a spunlace wipe of about 50 g/m$^2$ | 31.52 |
| 0.5% SLS | — | Sodium lauryl sulfate solution | 30.48 |

[1]Commercially available from Johnson & Johnson of New Brunswick, NJ
[2]Commercially available from Procter & Gamble of Cincinnati, Ohio
[3]As described in Table 1

Example III

The test compositions, E1, E2, C4 and C5 detailed below were prepared and impregnated onto a multi-layer spun lace wipe. All of these compositions below had the following ingredients: phenoxyethanol, 0.6%; glycerin, 0.18%; sodium hydroxide (30%) 0.2%, sodium benzoate, 0.5%; CARBOPOL ULTREZ, 0.2%; DERMOSOFT 688 (p-anisic acid) 0.06%, Fragrance 0.1%.

To make the various compositions, a vessel was charged with water. The CARBOPOL was added, then agitated. Sufficient NaOH was added to increase the pH to about 4.9 to about 5.2. A premix of all glycerin, and any of the required amounts of LAMESOFT PO 65, HISPAGEL 200, and EMULGIN VL-75 (see Table 2 below) was separately mixed at a temperature between ambient to about 50° C. and stirred for a time sufficient to homogenize the premix. The premix was then added to the water/polymer mixture and allowed to stir for a time sufficient to homogenize the mixture; then preservative was added and then the pH was adjusted to bring the pH to between 4.9 and 5.2. Comparative Example C1 is a PIT emulsion detailed above.

The particular percentages of LAMESOFT PO 65, HISPAGEL 200, and EMULGIN VL-75 as well as performance with respect to phase stability and cleansing are provided in Table 4 below:

TABLE 4

| Example | % LAMESOFT PO 65 | % HISPAGEL 200 | % EMULGIN VL-75 | Phase Stability | Cleansing, % | Comments[2] |
|---|---|---|---|---|---|---|
| E1 | 0.25% | 0.20% | 0.25% | PASS | 42% | Baseline |
| E2 | 0.70% | — | — | PASS | 39% | Not significantly different than baseline. |
| C4 | — | 0.70% | — | FAIL | 38% | Softer wipe than baseline |

TABLE 4-continued

| Example | % LAMESOFT PO 65 | % HISPAGEL 200 | % EMULGIN VL-75 | Phase Stability | Cleansing, % | Comments[2] |
|---|---|---|---|---|---|---|
| C5 | — | — | 0.70% | FAIL | 35% | Feels softer on skin than baseline |
| C1[1] | — | — | — | | 31% | |

[1]Comparative Example, C1 is described above with reference to Table 1
[2]Spunlace wipes were impregnated to 300% of the dry weight of the substrate with each of E1, E2, C4 and C5. Pairwise comparisons were conducted between E1 and each of E2, C4 and C5. Eleven panelists were asked which of the two wipes felt softer in the hands and softer on the skin. Softness differences having 99% statistical significance are reported.

Example IV

The following inventive examples shown in Table 5, consistent with embodiments of the invention described herein, were also prepared.

TABLE 5

Additional Inventive Examples

| Ingredient[1] | Percent By Weight | | | |
|---|---|---|---|---|
| | E3 | E4 | E5 | E6 |
| Water, deionized | 97.21 | 97.26 | 96.76 | 97.06 |
| HISPAGEL 200 | — | 0.2 | 0.2 | 0.2 |
| LAMESOFT PO 65 | 0.25 | 0.25 | 0.25 | 0.25 |
| EMULGIN VL 75 | 0.25 | 0.25 | 0.25 | 0.25 |
| PLANTACARE 818UP | — | — | 0.5 | — |
| Glycerin, 99.5% | 0.18 | 0.18 | 0.18 | 0.18 |
| Sodium hydroxide, 30% | 0.2 | 0.2 | 0.2 | 0.2 |
| Sodium benzoate | 0.5 | 0.5 | 0.5 | 0.5 |
| Phenoxyethanol | 0.6 | 0.6 | 0.6 | 0.6 |
| CARBOPOL ULTREZ 10 | 0.3 | 0.0 | 0.2 | 0.2 |
| CARBOPOL ULTREZ 20 | — | — | — | — |
| CARBOPOL ULTREZ 21 | — | 0.2 | — | — |
| NATROSOL 250HR | — | — | — | 0.2 |
| DERMOSOFT 688 (p-anisic acid) | 0.06 | 0.06 | 0.06 | 0.06 |
| Fragrance | 0.1 | 0.1 | 0.1 | 0.1 |
| Citric Acid | 0.2 | 0.2 | 0.2 | 0.2 |

[1]Supplier information for HISPAGEL, LAMESOFT, EMULGIN, PLANTACARE, CARBOPOL, and DERMOSOFT, as well as other ingredients are provided in the instant specification.

Cleansing Test

The following Cleansing Test was performed on the personal care compositions to determine the ability of the composition to cleanse the skin. The procedure was accomplished by marking an area (4 cm×4 cm) to be treated. An initial skin luminance reading (only the "whiteness" or "L" portion of the L, a, b component is recorded), $l_i$ is taken using a Minolta Chromameter CR 300, commercially available from Konica Minolta Sensing Americas of Ramsey, N.J. 0.08+/−0.02 grams of composition is placed on the skin and allowed to dry for 10 minutes. Another reading is taken and recorded as treated skin luminance, $l_t$. The area of the skin is then cleansed by placing a wipe (pre-impregnated with the particular composition) onto a cylinder of having a 120 mm height and a 40 mm diameter and placing the wipe. The particular 4 cm×4 cm are is then rotated 180° in order to wipe the skin. Pressure is kept at a constant pressure for all readings. The area of skin is allowed to dry and a final luminance reading, $l_c$ is taken. % Cleansing is calculated as $(l_t-l_r)/(l_c-l_t)$.

It can be concluded from the results of Example I and Example II above that surprisingly, it is possible to improve considerably on the cleansing of a PIT emulsion, (such as Comparative Example C1), while both drastically reducing the level of surfactant and emollient and maintaining mildness. Furthermore, it is possible to do this and achieve phase stability.

Furthermore it is possible to obtain these benefits while using surfactant and emollients that are primarily or entirely (such as alkyl glycerides and alkyl glucosides) ones that have a high regulatory acceptability. HISPAGEL (water-soluble glyceryl polyacrylate) and EMULGIN (polyol polyhydroxystearates) contribute to increased softness and can be formulated with alkyl glycerides and alkyl glucosides. It is further surprising that a blend, Example E1 of LAMESOFT, HISPAGEL and EMULGIN shows better cleansing than any of the LAMESOFT, HISPAGEL and EMULGIN alone.

Compositions of the present invention are particularly suited for use on wipes, particularly personal care wipes, and, even more particularly for baby wipes in order to achieve a high degree of cost-effectiveness and skin mildness.

The invention claimed is:

1. An article comprising a water-insoluble absorbent substrate wherein the substrate is at least one sheet of non-woven fabric and a composition impregnated therein wherein said composition comprises:
    (i) from about 97% to 99% water;
    (ii) a glyceryl polyacrylate in a concentration from about 25 ppm to about 5000 ppm;
    (iii) a non-ionic surfactant that is a $C_8$-$C_{20}$ alkyl glucoside;
    (iv) one or more hydrophobic emollients that are $C_{12}$-$C_{30}$ mono- or diglycerides present in a concentration from about 200 ppm to about 4000 ppm, and wherein the composition has a ratio of total surfactant concentration to total hydrophobic emollient concentration that is from about 0.5 to about 2.5.

2. The article of claim 1, wherein the composition is substantially free of anionic surfactants.

3. The article of claim 1, wherein the composition comprises a polyol humectant.

4. The article of claim 1, wherein the composition is impregnated onto said nonwoven fabric to a weight percentage of from about 100% to about 400% relative to the nonwoven fabric.

* * * * *